United States Patent [19]

Giambalvo

[11] 4,223,782
[45] Sep. 23, 1980

[54] CONTACT LENS CLEANING AND RINSING DEVICE AND METHOD

[75] Inventor: Melcheore F. Giambalvo, York, Pa.

[73] Assignees: George D. Weaver; Scott S. Weaver, both of York, Pa.; part interest to each

[21] Appl. No.: 14,334

[22] Filed: Feb. 23, 1979

[51] Int. Cl.³ .................. A45C 11/04; B08H 3/04
[52] U.S. Cl. .................. 206/5.1; 294/64 R
[58] Field of Search .................. 206/5.1, 424.8; 294/64 R, 1 CA; 134/199

[56] References Cited

U.S. PATENT DOCUMENTS

| | | | |
|---|---|---|---|
| 3,091,328 | 5/1963 | Leonardos | 206/5.1 |
| 3,442,707 | 5/1969 | Dzedzej | 134/199 |
| 3,822,780 | 7/1974 | Ulmer et al. | 206/5.1 |
| 3,879,076 | 4/1975 | Barnett | 294/64 R |

FOREIGN PATENT DOCUMENTS 1431168  4/1976  United Kingdom .................. 294/1 CA Primary Examiner—William T. Dixson, Jr.
Attorney, Agent, or Firm—Samuel M. Learned, Jr.

[57] ABSTRACT

A contact lens cleaning and rinsing device comprised of a vacuum tool for conveniently retaining a preferably soft contact lens in a positively held position for sequential chemical cleaning and rinsing of both sides thereof prepatory to either thermal or chemical disinfecting of the lens prior to eye contact application and use by the wearer.

3 Claims, 14 Drawing Figures

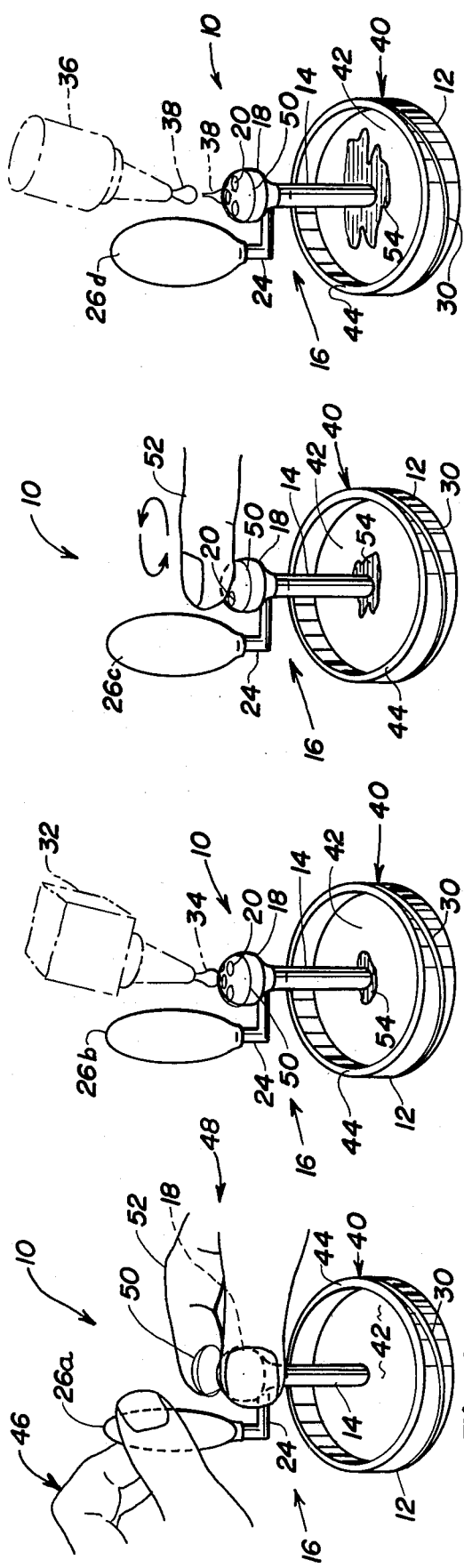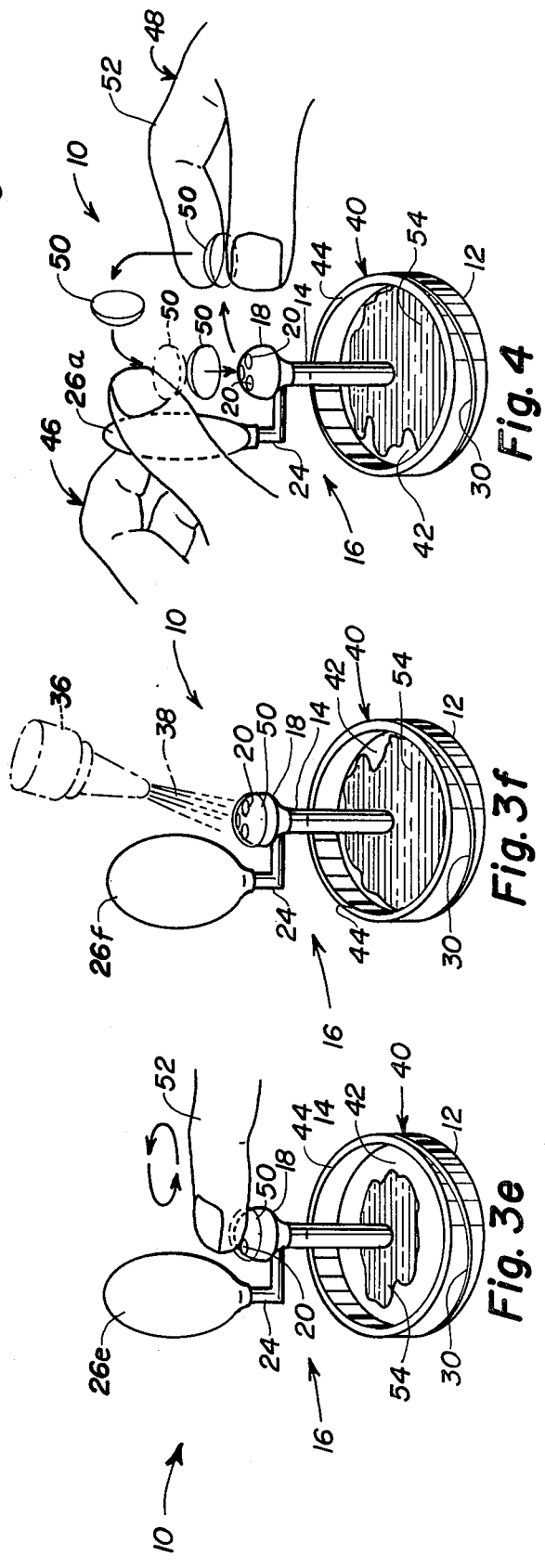

CONTACT LENS CLEANING AND RINSING DEVICE AND METHOD

BACKGROUND OF THE INVENTION

The instant invention relates to a vacuum tool whereby a contact lens wearer not possessed of special skills or training, through employment of the same, is provided with a relatively simple device for retaining in a positively held position a contact lens during sequential accomplishment of the normally necessary contact lens cleaning and rinsing maintenance functions, properly and completely, prepatory to lens disinfecting operations, and prior to eye contact application and use of contact lens apparatus by the wearer thereof.

It is to be understood that the present invention discloses a contact lens cleaning and rinsing device principally applicable to use in the routine cleaning and rinsing maintenance of deformable or so-called soft contact lenses, however, it is to be further understood that there is also an incidental application adaptation of the device as herein taught to the cleaning and rinsing maintenance of the rigid or so-called hard contact lenses.

Among the more recent developments in contact lens art is that of soft contact lenses, fabricated from pliable protein materials, with certain enhanced use, convenience, and comfort features obtained thereby for persons who wear such vision correction apparatus relative to the optional use of hard contact lenses. However, since soft contact lenses are made from protein materials the substance thereof is subject to biodegradable deterioration if the wearer does not properly perform those recommended daily maintenance routines of cleaning, rinsing, and disinfecting the lenses between use applications. Also, the very delicate nature of the soft contact lens material makes it more susceptible to scratching or other damage if cleaning and rinsing technique is by methods otherwise suitable for hard contact lens maintenance, and further, since there is a protein interface between the lens contact surface and the eye of the wearer, which is also a proteinaceous substance, proper cleaning and rinsing of the soft contact lens, to substantially remove all cleaning solution chemicals so as not to cause eye irritation to the wearer, is of paramount importance and necessity.

In the past, contact lens cleaning and maintenance was accomplished by rather haphazard methods, such as simply rinsing the lenses under a stream of tap water, with the result that lenses were not properly cleaned and were frequently broken or lost down a sink drain. As the need for more suitable and effective contact lens cleaning and rinsing technique became apparent, and since such functions are normally accomplished by the contact lens wearer on a routine daily basis, the development of various devices evolved to meet that need.

In general, the prior art contact lens cleaning and rinsing devices are comprised of the following major types. First, a relatively simple tap water/chemical flushing of a pair of contact lenses retained in open-structure retaining baskets, exemplary of which is that as taught in U.S. Pat. No. 3,586,012 to Paule, dated June 22, 1971.

A second general type of contact lens cleaning and rinsing device embodies various versions of mechanical cleaning means, such as cleaning solution circulation as respectively taught in U.S. Pat. No. 3,115,146 to Erwin, dated Dec. 24, 1963, and U.S. Pat. No. 3,444,868 to Hungerford et al, dated May 20, 1969, or squeeze bottle cleaning solution circulation as taught in U.S. Pat. No. 3,113,579 to Willis, dated Dec. 10, 1963. Additional mechanical cleaning means methods would be reciprocating agitation of the lenses within a cleaning solution container as respectively taught in U.S. Pat. No. 2,944,661 to Goldstein, dated July 12, 1960, or to Hungerford et al in U.S. Pat. No. 3,279,482 dated Oct. 18, 1966, or mechanical agitation of the lens per se within a cleaning solution chamber as taught in U.S. Pat. No. 3,623,492 to Frantz et al, dated Nov. 30, 1971, and alternately, by way of mechanical circulation of the cleaning solution about the lenses when retained in suitable open-structure retaining baskets in a cleaning solution chamber as taught in U.S. Pat. No. 3,614,959 to Schollmaier et al, dated Oct. 26, 1971. Another method of mechanical cleaning would be as taught in U.S. Pat. No. 3,150,406 to Obitts, dated Sept. 29, 1964, wherein a contact lens is retained within a lens holding tong and reciprocally moved through a cleaning solution saturated sponge.

A third general type of contact lens cleaning and rinsing device utilizes means for aerosol application of a cleaning solution to contact lenses held in open-structure retaining basket supports as taught in U.S. Pat. No. 3,856,571 to Sherman, dated Dec. 24, 1974.

Lastly, a fourth general type of contact lens cleaning and rinsing device employs ultrasonic means as respectively taught in U.S. Pat. No. 3,640,294 to Piccolo, dated Feb. 8, 1972, and U.S. Pat. No. 3,871,395 to Murry, dated Mar. 18, 1975.

It should be understood that some of the features of the instant invention have, in some cases, certain structural and functional similarities to teachings separately set forth in other prior art disclosures, such as the structure and method taught in U.S. Pat. No. 3,343,657 to Speshyock, dated Sept. 26, 1967, the lens support structures respectively taught in U.S. Pat. No. 3,822,780 to Ulmer et al, dated July 9, 1974, and U.S. Pat. No. 4,091,917 to Clawson et al, dated May 30, 1978, or vacuum chuck lens holding means as taught in U.S. Pat. No. 3,794,314 to Coburn et al, dated Feb. 26, 1974. However, as will hereinafter be pointed out, the instant invention is distinguishable from said earlier inventions in one or more ways in that the present invention has utility features and new and useful advantages, applications, and improvements in the art of contact lens cleaning and rinsing devices not heretofore known.

SUMMARY OF THE INVENTION

It is the principal object of the present invention to provide a contact lens cleaning and rinsing device comprised of a supporting base member upon which is assembled a vertically projecting vacuum head assembly whereby a deformable or so-called soft contact lens may be positively retained in a securely held position upon the vacuum head contact/support surface thereof through a differential pressure force created by means of said vacuum head assembly, being between the ambient atmospheric pressure and the lens sealing vacuum head contact/support surface reduced pressure, such that a contact lens wearer may thus be enabled to simply accomplish the speedy, safe, and efficient cleaning and rinsing, sequentially of one side of said soft contact lens and then the other, with but a single lens removal and replacement handling operation therebetween with respect to use of said device for the purpose of accomplishing contact lens cleaning and rinsing operations prepatory to lens disinfecting by either the so-called HOT (thermal) or COLD (chemical) methods.

A further object of the present invention is to provide a contact lens cleaning and rinsing device adapted to universally accommodate soft contact lenses of different diameters dimensioned within the normal prescription diameter ranges as well as also soft contact lenses of different radii of curvature configured within the normal prescription radius ranges.

It is another object of the present invention to provide a contact lens cleaning and rinsing device whereby the use thereof enables substantially the complete rinsing of cleaning solution and residue from the cleaned contact lens surfaces, thereby also substantially eliminating by more effective rinsable removal substances from the lens surfaces which might otherwise be either damaging to the lens material or harmful to the eye of the wearer thereof when the lens is applied to the surface of the eye in use application.

It is a further object of the present invention to provide a contact lens cleaning and rinsing device whereby the use thereof, and the effectiveness of the cleaning and rinsing of the lens surfaces accomplished thereby, enables employment of the chemical (COLD) lens disinfecting process, which is the simpler and less expensive, and therefore preferred, method for accomplishing lens disinfecting after cleaning and rinsing, as opposed to the thermal (HOT) method which employs a boiling solution in relatively costly and complicated electromechanical equipment rather than a simple soaking of the cleaned and rinsed lens in a cold disinfectant solution.

Still another object of the present invention is to provide a contact lens cleaning and rinsing device whereby the use thereof reduces significantly the probability of loss as well as also that of damage, by scratching or otherwise, of the contact lens during the accomplishment of cleaning and rinsing operations.

It is yet another object of the present invention to provide a contact lens cleaning and rinsing device, whereby an average person not possessed of special skills or training may properly and effectively employ the same in an accomplishment of the normally necessary contact lens cleaning and rinsing maintenance functions.

It is an additional object of the present invention to provide a contact lens cleaning and rinsing device embodying materials of construction which are preferably substantially inert to chemical reaction with lens materials of construction as well as also commercially available lens cleaning and rinsing solution materials.

Yet another object of the contact lens cleaning and rinsing device of the present invention is to incidentally accommodate vacuum holding of a rigid or so-called hard contact lens for purposes of accomplishing the cleaning and rinsing of the convex side thereof.

Another object of the present invention is to provide a contact lens cleaning and rinsing device provided with a supporting base member adapted to receive and retain waste cleaning and rinsing solution materials during the conduct of contact lens cleaning and rinsing operations by the employment of said device, in addition to having a supporting base member further adapted to threadably receive a transparent protective cover member and conveniently secure therewithin upon said supporting base member suitable receptacles respectively containing cleaning and rinsing solutions during times of non-use of said device.

Details of the foregoing objects and the invention, as well as other objects thereof are set forth in the following specification and illustrated in the accompanying drawings comprising a part thereof.

BRIEF DESCRIPTION OF THE DRAWINGS

FIG. 3a is a front perspective view of the contact lens cleaning and rinsing device per se, showing the method for securing an exemplary soft contact lens thereto for purposes of accomplishing cleaning and rinsing operations on one side thereof.

FIG. 3b is a front perspective view of the contact lens cleaning and rinsing device per se, with an exemplary soft contact lens secured thereto, showing the method for applying cleaning solution.

FIG. 3c is a front perspective view of the contact lens cleaning and rinsing device as illustrated in FIG. 3b, showing the method for accomplishing contact lens cleaning.

FIG. 3d is a front perspective view of the contact lens cleaning and rinsing device as illustrated in FIG. 3c, showing the method for applying rinsing solution.

FIG. 3e is a front perspective view of the contact lens cleaning and rinsing device as illustrated in FIG. 3d, showing the method for accomplishing initial contact lens rinsing.

FIG. 3f is a front perspective view of the contact lens cleaning and rinsing device as illustrated in FIG. 3e, showing the method for accomplishing final contact lens rinsing.

FIG. 4 is a front perspective view of the contact lens cleaning and rinsing device as respectively illustrated in FIG. 3a through FIG. 3f inclusive, but, however, showing the method of removing, inverting, and replacing an exemplary soft contact lens thereto for purposes of accomplishing cleaning and rinsing operations on the other side thereof by that method heretofore illustrated in said FIGS. 3a through 3f inclusive.

DETAILED DESCRIPTION OF THE INVENTION

Figure 1:
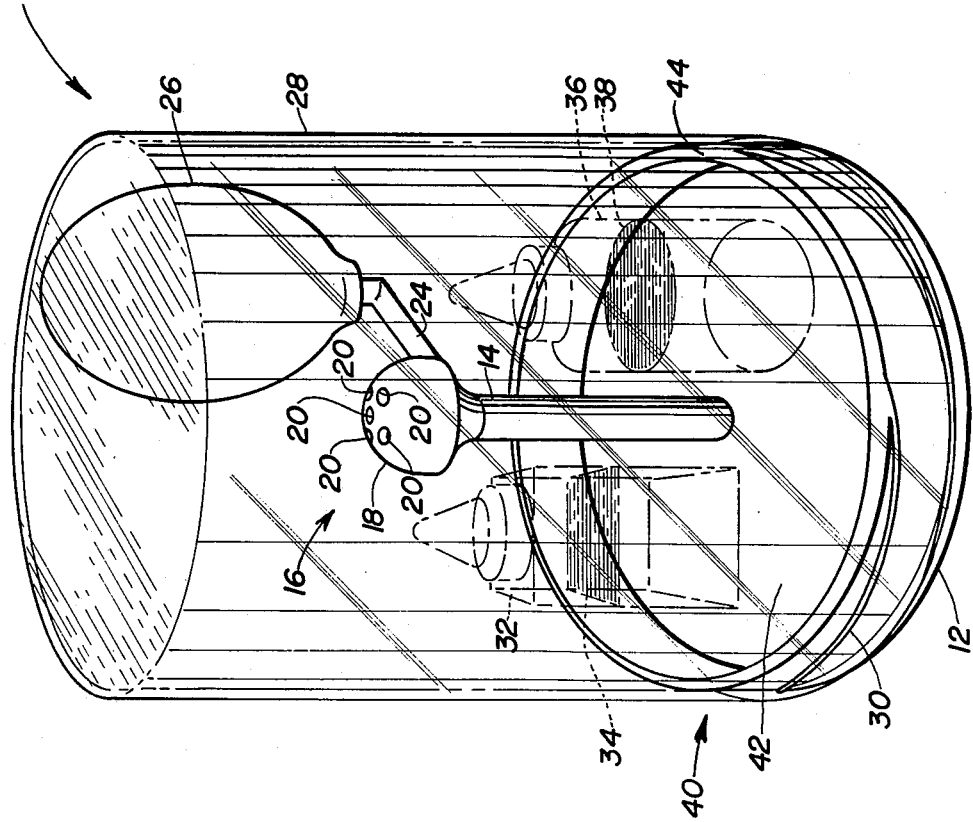
FIG. 1 is a front perspective view of the contact lens cleaning and rinsing device assembly embodying the principles of the present invention, being shown in the storage condition.

Referring to FIG. 1, the present invention is shown which comprises a contact lens cleaning and rinsing device 10, said device 10 having a supporting base member 12 from which centrally intermediate thereof upwardly extends a vacuum head assembly support shaft 14 having fixedly assembled to the upward terminal end thereupon a vacuum head assembly 16 further comprising a vacuum head contact support surface 18 axially provided with a plurality of radially spaced vacuum port openings 20 communicating from said vacuum head contact support surface 18 by way of the vacuum head manifold 22 (not shown in FIG. 1, but illustrated in FIG. 2 and certain subsequent Figures) through vacuum respirator conduit 24 to the vacuum respirator bulb 26, whereby a contact lens for cleaning and rinsing operations, as hereinafter more fully described, is secured and supportively retained in position during said cleaning operations, all of which vacuum head assembly 16 structure is protectively enclosed within a transparent cover member 28 removably affixed in threadable communication to said supporting base member 12 by twist threads 30, in illustration of said device 10 in the storage configuration when the same is either not in use or in transport between use application employment thereof.

Although not comprising a part of the instant invention per se, also shown in phantom in FIG. 1 are respectively an exemplary contact lens cleaning solution container 32 wherein is retained a suitable exemplary contact lens cleaning solution 34, and an exemplary contact lens rinsing solution container 36 wherein is retained a suitable exemplary contact lens rinsing solution 38, the illustration of which exemplary containers is presently for convenience primarily to show how said containers 32 and 36 may, for more immediate facility in use employment of said device 10 in accomplishing contact lens cleaning and rinsing operations, be positioned upon said supporting base member 12 and secured thereupon by enclosement within the transparent cover member 28 when the same is assembled to said supporting base member 12 in threadable communication therewith. Additionally, in setting forth a subsequent detailed description of the method of employment of said device 10 in accomplishing the sequence of contact lens cleaning and rinsing, as shown in illustration series FIG. 3a through FIG. 3f hereof, it is necessary to show also the employment respectively of an exemplary contact lens cleaning and rinsing solution material.

Figure 2:
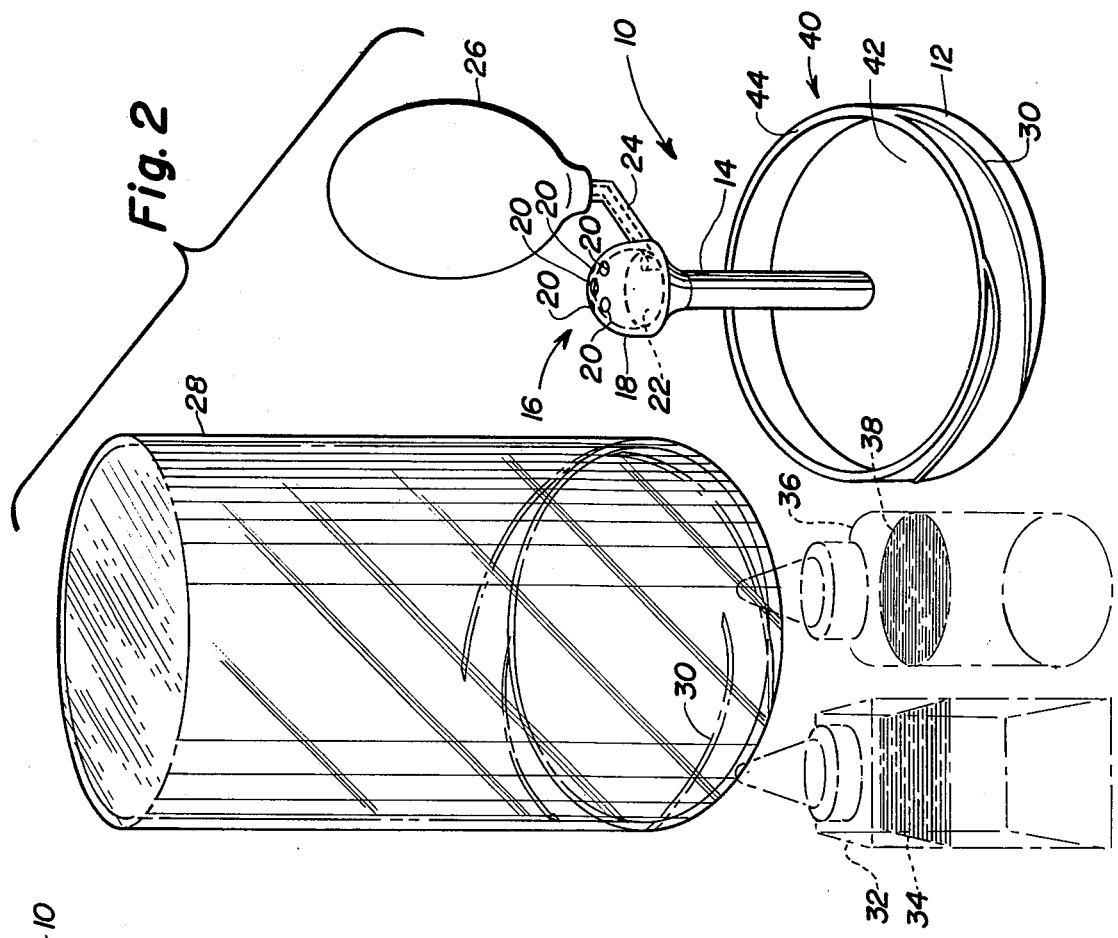
FIG. 2 is a front perspective view of the contact lens cleaning and rinsing device assembly components as shown in FIG. 1, but herein illustrated as being separated for contact lens cleaning and rinsing use application.

Referring now to FIG. 2, being a perspective view of the device 10 configured for contact lens cleaning and rinsing use application employment, with the transparent cover member 28 thereof removed and the exemplary contact lens cleaning solution container 32 and exemplary contact lens rinsing solution container 36 being set aside, wherein there is better illustrated a waste cleaning and rinsing solution collection reservoir structure 40 of the supporting base member 12 formed by the upwardly disposed base surface 42 and upwardly extending radially peripheral twist thread support wall 44 communicating therewith, whereby spent cleaning and rinsing solution materials are received and conveniently retained during and through contact lens cleaning operations, thereby eliminating the mess and bother of waste solution collection and disposal which would otherwise be encountered were not such a waste cleaning and rinsing solution collection reservoir structure 40 provided. With the device 10 transparent cover member 28 removed as shown in FIG. 2, and the exemplary contact lens cleaning solution container 32 and rinsing solution container 36 respectively set aside from the storage or transport configuration as previously illustrated in FIG. 1, said device 10 is thereupon readied for contact lens cleaning and rinsing operations employing the same by that procedure as hereinafter described.

Figure 7:
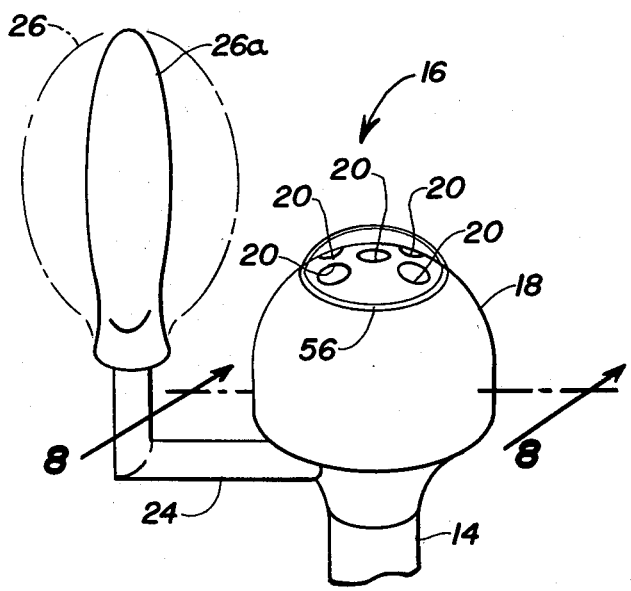
FIG. 7 is an enlarged perspective elevation of the vacuum head assembly of the contact lens cleaning and rinsing device of the instant invention, illustrating therein the securement of an exemplary hard contact lens to the vacuum head thereof for incidental use application of said device in accomplishing cleaning and rinsing operations of the convex side thereof.
Figure 8:
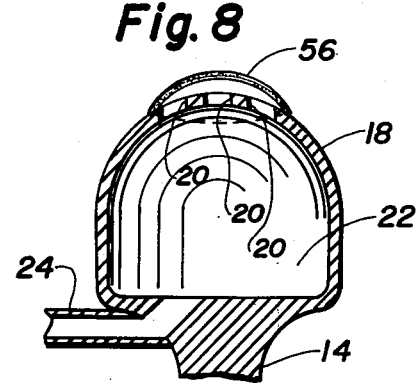
FIG. 8 is a side sectional elevation of the vacuum head as shown generally in FIG. 7 and seen along the line 8—8 thereof.

Prior to proceeding in further detailed description of the contact lens cleaning and rinsing device herein taught, it should be again mentioned, as previously set forth, that said device has primary application to the cleaning and rinsing of so-called soft contact lenses having pliable properties with certain limited use application thereof to the cleaning and rinsing of so-called hard contact lenses not having pliable properties, the accomplishment of which cleaning and rinsing operations is performed by the wearer/user upon either lens type prepatory to subsequent lens disinfecting operations by either the HOT (thermal) or COLD (chemical) methods, all of which comprises currently normal recommended contact lens daily maintenance procedures in the hygienically safe use thereof. In the foregoing regard, FIGS. 3a through 6b hereinafter, and the detailed descriptions thereof are applicable to said device as employed in the cleaning and rinsing operations accomplished thereby upon soft contact lenses; wherein FIGS. 7 and 8 illustrate the employment of said device as applicable to the more limited use thereof in accomplishing hard contact lens cleaning and rinsing operations.

Referring now to illustration series FIGS. 3a through 3f, and FIG. 4 hereof, in consideration of the device herein taught as applicable to soft contact lens cleaning and rinsing, in view of which the following should be pointed out. First, the primary utility feature of the device 10 as herein taught is that the same provides a simple and effective means whereby a contact lens wearer may, through employment thereof, properly secure a contact lens upon a supportively retaining work surface, that is, upon the vacuum head contact support surface 18 of said device 10, by differential pressure vacuum adherence means, such that the lens to be cleaned and rinsed is thereby immobilized and made conveniently accessable for purposes of accomplishing the cleaning and rinsing thereof. Second, as a result of the proper supportive retention and immobilization of a contact lens upon a convenient and accessable work surface as provided by said device 10, the hazards of loss or damage to a contact lens during accomplishment of cleaning and rinsing thereof is substantially eliminated, and, equally, if not more important, proper and effective lens cleaning, and the substantially complete rinsable purging of cleaning solution materials from the lens surface is enabled so as not to thereafter cause subsequent eye irritation problems to the lens user as a result of residual lens surface cleaning solution contamination, is likewise also substantially eliminated.

Considering now in detail the employment of said device 10, as sequentially illustrated in FIGS. series 3a through 3f inclusive, in application thereof to soft contact lens cleaning and rinsing operations, wherein it will be understood that a lens for cleaning and rinsing operations will have immediately prior thereto been removed from contact adherence to an eye of the wearer thereof such that said lens will be coated with a film of eye fluids whereby vacuum sealing thereof to the vacuum head contact support surface 18 of said device 10, as hereinafter more fully described, will be facilitated.

The soft contact lens wearer/user of said device 10, with the same in the soft contact lens cleaning and rinsing use application configuration as shown in FIG. 3a, thereupon with a first hand 46 compresses the vacuum respirator bulb 26 to an evacuated respirator bulb configuration as represented by 26a, thereby creating a reduced pressure differential potential within the vacuum head manifold 22 (previously illustrated in FIG. 2) of the vacuum head assembly 16 internally thereof throughout by way of the vacuum respirator conduit 24 enclosably communicating with said bulb 26, which in turn creates an external reduced pressure differential potential at the vacuum head contact support surface 18 through the plurality of radially spaced vacuum port openings 20 communicating from said manifold 22 to said support surface 18, and simultaneously therewith, with a second hand 48 containing a soft contact lens 50, which immediately previous thereto had been removed from eye contact of the wearer thereof such that the surfaces of said soft contact lens 50 are coated with a film of eye fluids, positions said soft contact lens 50 with the concave surface side thereof for application to the upwardly conforming convexly curved vacuum head contact support surface 18, whereupon said lens 50 is applied by index finger 52 pressure of the second hand 48 such that the concave surface thereof axially communicates to the conforming convex vacuum head contact support surface 18 and is thereupon sealably adhered thereto by the lens coating film of eye fluids, at which time the wearer/user releases the first hand 46 vacuum respirator bulb compression pressure previously applied and the vacuum pressure differential force thus created upon opposing sides of the soft contact lens thereby effects supportive retention and immobilization of said soft contact lens 50 in a position such that the upwardly disposed convex side thereof is fully exposed in an openly accessible position upon the vacuum head contact support surface 18 so that cleaning and rinsing operations upon the upwardly disposed convex side of said lens 50 may be commenced. It should be noted that the vacuum seal created between the convex lens side and the vacuum head contact support surface 18 is not, in practice, by means of device 10 as herein taught, absolute, and the vacuum will dissipate within a period of some thirty to sixty seconds as respectively illustrated by increasing vacuum respirator bulb expansion 26b through 26f in corresponding FIGS. 3b through 3f, which time of vacuum seal duration as recited, however, is more than sufficient for a normal wearer/user of device 10, not possessed of special skill or ability, to properly accomplish lens cleaning and rinsing operations on one side of a soft contact lens 50 as herein recited through employment of said device 10.

With the soft contact lens 50 supportively retained by vacuum differential pressure upon the vacuum head contact support surface 18 as above-described, and more clearly illustrated in FIG. 3b, the wearer/user dispenses from the exemplary contact lens cleaning solution container 32, upon the upwardly disposed convex side of said soft contact lens 50 several drops of exemplary contact lens cleaning solution 34 prepatory to index finger 52 rotary agitation thereof upon the soft contact lens 50 surface being cleaned, the waste solution portion 54 of which cleaning solution 34 drains downwardly and is collectably retained within the waste cleaning and rinsing solution collection reservoir structure 40 of the supporting base member 12.

Next, as illustrated in FIG. 3c, the wearer/user, employing index finger 52, applies rotary agitation motion as shown to the exemplary contact lens cleaning solution 34 previously applied to the soft contact lens 50 surface to be cleaned, thereby completing removal of eye fluid and foreign matter from the upwardly disposed soft contact lens 50 exposed surface.

Following completion of index finger rotary agitation motion of exemplary contact lens cleaning solution 34 upon the soft contact lens 50 surface being cleaned, as illustrated in FIG. 3d, wearer/user dispensement from the exemplary contact lens rinsing solution container 36, upon the upwardly disposed convex side of said soft contact lens 50 as previously cleaned, several drops of exemplary contact lens rinsing solution 38 prepatory to index finger 52 rotary agitation thereof upon the soft contact lens 50 surface being rinsed, wherein again, the waste solution portion 54 of which rinsing solution 38 drains downwardly and is collectably retained within the waste cleaning and rinsing solution collection reservoir structure 40 as previously described.

In order to facilitate rinsable removal of previously cleaned eye fluid and foreign matter, as well as also cleaning solution material 34 from the soft contact lens 50 surface, the wearer/user, as illustrated in FIG. 3e, next, again employing index finger 52, applies rotary agitation motion to the exemplary contact lens rinsing solution 38 previously applied to the soft contact lens 50 surface to be rinsed, thereby substantially removing cleaning residues and materials from the upwardly disposed soft contact lens 50 exposed surface. However, to insure substantially thorough rinsing, as illustrated in FIG. 3f, the wearer/user lastly dispenses from the exemplary contact lens rinsing solution container 36 a flushing rinse spray of exemplary contact lens rinsing solution 38 upon the upwardly disposed soft contact lens 50 surface as previously cleaned and pre-rinsed during those procedure steps illustrated and described in FIGS. 3b through 3e hereof above.

The means of accomplishing cleaning and rinsing of the reverse side of a soft contact lens 50 is exactly as above described with respect to the device 10 and the procedure set forth as illustrated in FIGS. 3a through 3f hereof, wherein FIG. 4 illustrates removal, flex-inversion of the pliable soft contact lens 50 so that the concave side thereof is reversed, and re-application of said soft contact lens 50 to the vacuum head contact surface so that the other side thereof may be cleaned and rinsed prepatory to disinfecting of the same by either thermal or chemical methods.

With regard to contact lens disinfecting means and methods, which is likewise not per se a part of the device and method disclosure herein taught, it is, notwithstanding, worthy of mention that the effectiveness of the soft contact lens cleaning and rinsing results achievable by use of the device as herein taught are sufficient so as to enable the employment of cold chemical disinfectant procedures which are preferable to the thermal disinfectant procedures as applied to soft contact lenses in that the cold chemical disinfectant procedures, although generally not as effective if proper contact lens cleaning and rinsing are not achieved, are otherwise just as effective as the thermal disinfectant procedures and much less deleterious to the fragile soft contact lens material.

Figure 5:
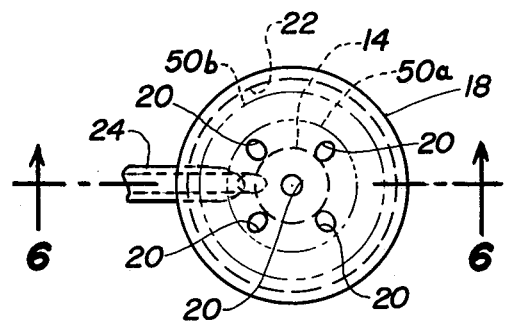
FIG. 5 is an enlarged plan view of the vacuum head surface of the contact lens cleaning and rinsing device of the instant invention, showing in phantom respectively the smallest and the largest diameter exemplary soft contact lenses which may be accommodated in secured affixment thereto.

Turning now to a consideration of FIG. 5, which is a plan view illustrating how the vacuum head contact support surface 18 and the radially spaced vacuum port openings 20 thereof are adapted to accommodate soft contact lenses of different diameters, wherein the nominally smallest diameter soft contact lens 50a which may be accommodated thereto in terms of providing a sufficient area to effect sealing of the axial array of radially spaced vacuum port openings 20 is 10-millimeters and the nominally largest diameter soft contact lens 50b which may be accommodated thereto in terms of fitting the vacuum head contact support surface 18 is 18-millimeters, which encompasses the normal range of soft contact lens diameters generally prescribed, wherein the nominal diameter of the outer peripheral opening dimension of the axial array of radially spaced vacuum port openings 20 is 8-millimeters with the vacuum port openings 20 per se each having an optimal diameter opening of 2.0-millimeters but operable within an opening diameter range of from 0.1 to 2.5-millimeters, and the nominal diameter of the vacuum head contact support surface 18 being 20-millimeters.

Figure 6A:
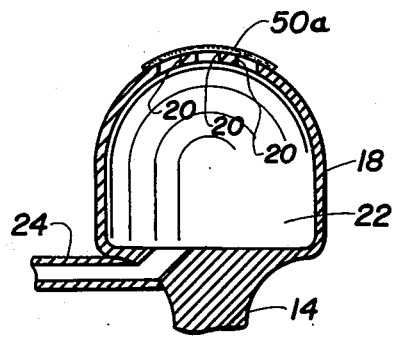
FIG. 6a is a side sectional elevation of the vacuum head as shown generally in FIG. 5 and seen along the line 6—6 thereof, illustrating therein the smallest diameter exemplary soft contact lens which may be accommodated in secured affixment thereto for the accomplishment of cleaning and rinsing operations.
Figure 6B:
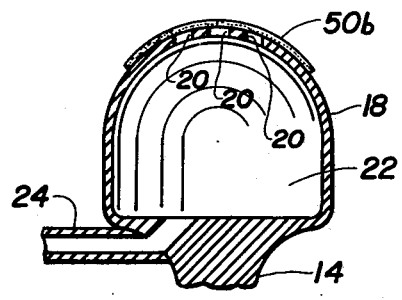
FIG. 6b is a side sectional elevation of the vacuum head as shown generally in FIG. 5 and seen along the line 6—6 thereof, illustrating therein the largest diameter exemplary soft contact lens which may be accommodated in secured affixment thereto for the accomplishment of cleaning and rinsing operations.

The view illustrated in FIG. 6a is a side sectional elevation of the plan view seen in FIG. 5, showing therein side elevation accommodation of the nominally smallest diameter soft contact lens 50a to the vacuum head contact support surface 18, and FIG. 6b is a similar side sectional elevation of the plan view seen in FIG. 5, showing alternately therein however side elevation accommodation of the nominally largest diameter soft contact lens 50b to the vacuum head contact support surface 18, wherein the nominally smallest diameter contact lens 50a also illustrates the smallest normal radius of curvature of a soft contact lens that being 40-diopters and the nominally largest diameter contact lens 50b also illustrates the largest normal radius of curvature of a soft contact lens that being 48-diopters such that it may also be seen that said vacuum head contact support surface 18 is further adapted to accommodate soft contact lenses within the normal radius of curvature range thereof, that is, between 40 to 48-diopters, which is enabled by the pliable nature of a soft contact lens in addition to said vacuum head contact support surface 18 being provided with an optimal radius of curvature for the 40 to 48-diopter range of 8.4-millimeters but being accommodatingly operable in the foregoing respect within a radius of curvature range of from 7.6 to 12.0-millimeters.

The contact lens cleaning and rinsing device 10 as herein disclosed and described is preferably cast-constructed from chemically inert material such as certain of various metals or plastics or combinations thereof, however, any other suitable materials or combinations thereof, or construction methods or combinations thereof, may be used or employed.

Considering lastly the incidental or limited use application of said device 10 to hard contact lens cleaning and rinsing, as respectively illustrated in FIGS. 7 and 8, therein showing the vacuum adherence of an exemplary hard contact lens 56 to the vacuum head contact support surface 18, and showing also, as a result of the non-pliable nature of said exemplary hard contact lens 56, the vacuum adherence configuration thereof to said vacuum head contact support surface 18. As is apparent upon inspection of those illustrations of instant consideration, because of the rigid hard contact lens structure, only certain of such lenses, depending upon the diameters and radii of curvature thereof, would be suitable for cleaning and rinsing use accommodation with said device 10. Also, since a hard contact lens is not adapted for flex-inversion to reverse the concave side thereof, only one side, the fixed convex side of an exemplary hard contact lens 56, may be cleaned and rinsed by use employment in application of the device 10 as herein taught, by that procedure as previously described with respect to said device 10 as set forth and illustrated in FIGS. 3a through 3f hereof.

Although the invention has been herein shown and described in what is conceived to be the most practical and preferred embodiment, it is recognized that departures may be made therefrom within the scope of the invention, which is not to be limited to the details disclosed herein but is to be accorded the full scope of the claims so as to embrace any and all equivalent devices and apparatus.

I claim:

1. A contact lens cleaning and rinsing device to retain a contact lens in securely held position for application of cleaning and rinsing solution materials thereto in an accomplishment of cleaning and rinsing maintenance functions to be performed thereupon, said device comprising in combination a vacuum head assembly adapted to receive and retain in close sealed temporary vacuum communication therewith said contact lens, said vacuum head assembly supportably disposed upon the upward terminal end of a vertically projecting vacuum head assembly support shaft affixed at the lower vertical end thereof centrally intermediate and on axial alignment of a supporting base member wherein said vacuum head assembly further comprises, a vacuum head contact support surface radially configured convexly upward to generally conform with a concave surface of said contact lens, a plurality of radially spaced vacuum port openings disposed circumferentially of said vacuum head contact support surface axially thereof and circumferentially therewithin and communicating from said surface downwardly to within an enclosed vacuum manifold, said vacuum manifold in turn enclosably communicating to a vacuum respirator bulb by means of an enclosed vacuum respirator conduit interposed therebetween whereby upon an application of compressive pressure to said vacuum respirator bulb, thereby substantially evacuating the same, a differential vacuum pressure potential relative to an existing ambient pressure condition is thus created upon said vacuum head contact support surface through said communicating radially spaced vacuum port openings such that upon application of said contact lens by way of the concave surface thereof to said vacuum head contact support surface, and upon a release of said application of compressive pressure to said vacuum respirator bulb, said contact lens is temporarily sealed immobily upon said vacuum head contact support surface with the convex side of said contact lens thereby being openly disposed for said accomplishment of cleaning and rinsing maintenance functions to be performed thereupon, wherein said supporting base member is in the geometric form of a circular shape having an upwardly disposed base surface of uniform thickness throughout in which said upwardly disposed base surface is provided with a vertically upward extending side wall of a uniform elevation communicating therewith peripheral thereabout, said elevation being greater than that of said upwardly disposed base surface of uniform thickness but less than that of the upward terminal end of said vertically projecting vacuum head assembly support shaft to thereby provide a waste cleaning and rinsing solution collection reservoir.

2. The contact lens cleaning and rinsing device according to claim 1 in which said vertically upward extending side wall has an outward circumferential surface provided with a plurality of twist threads.

3. The contact lens cleaning and rinsing device according to claim 2 further including a transparent cover member having a plurality of mating twist threads communicable with said twist threads.

* * * * *